United States Patent [19]

Jones

[11] Patent Number: 4,682,591
[45] Date of Patent: Jul. 28, 1987

[54] RESUSCITATOR/VENTILATOR

[75] Inventor: Norman S. Jones, Leighton Buzzard, England

[73] Assignee: Pneupac Limited, London, England

[21] Appl. No.: 857,936

[22] Filed: Apr. 30, 1986

[30] Foreign Application Priority Data

May 2, 1985 [GB] United Kingdom ............ 8511170

[51] Int. Cl.⁴ .............................................. A61M 16/00
[52] U.S. Cl. .......................... 128/204.25; 128/205.11
[58] Field of Search ...................... 128/204.24, 204.25, 128/205.11, 205.24; 137/599.1, 606

[56] References Cited

U.S. PATENT DOCUMENTS

| 3,485,243 | 12/1969 | Bird et al. | 128/204.25 |
| 3,762,408 | 10/1973 | Cox et al. | 137/599.1 |
| 3,881,480 | 5/1975 | Lafourcade | 128/204.25 |
| 4,186,737 | 2/1980 | Valenta et al. | 128/204.24 |
| 4,401,115 | 8/1983 | Monnier | 128/204.25 |
| 4,401,116 | 8/1983 | Fry et al. | 128/205.24 |

FOREIGN PATENT DOCUMENTS 381353 10/1973 U.S.S.R. ......................... 128/204.25

Primary Examiner—Henry J. Recla
Attorney, Agent, or Firm—Arnold B. Silverman

[57] ABSTRACT

A portable resuscitator/ventilator device especially intended for emergency use and powered by pressurized primary breathable gas such as oxygen or compressed air from a bottle comprises a control unit that outputs primary gas pulses to a patient valve that includes an entrainment mixer for diluting the primary gas with air. The entrainment mixer is selectively operable to that the patient valve delivers primary gas or air-diluted primary gas as required. The control unit includes a fixed value flow-control restrictor that passes a required tidal volume of primary gas for undiluted delivery to the patient and the impedance of the patient valve is arranged to increase when the entrainment mixer is operational so that flow of the primary gas is automatically reduced to provide the required tidal volume of air-diluted primary gas without wastage of primary gas or any adjustment of the control unit.

7 Claims, 7 Drawing Figures

RESUSCITATOR/VENTILATOR

FIELD OF THE INVENTION

This invention concerns resuscitator/ventilator devices of the type powered by pressurised breathable gas such as compressed air or oxygen and adapted to deliver pulses of this gas to the respiratory passages of a patient to accomplish forced ventilation of the lungs in cases of respiratory failure or impairment.

BACKGROUND OF THE INVENTION AND PRIOR ART

Resuscitator/ventilator devices of this type, hereinafter termed, shortly, "gas-powered resuscitator/ventilator devices" typically include a control unit that generates the required pulses of breathable gas, and a so-called "patient valve" that is connected to the control unit by a flexible conduit or hose and that is associated with an oronasal mask or tracheal intubation device, this patient valve operating to connect the respiratory passages of the patient to the control unit during an inhalation phase, and to an exhaust outlet during the exhalation phase. Devices of this type in compact portable form are widely available to Emergency Services such as ambulance crews for resuscitation and short-term ventilation purposes, the devices in this form being almost invariably designed to deliver pulses of pure oxygen from a compressed oxygen source because not only is pure oxygen ventilation beneficial for short-term application such as in resuscitation, but its use in this way permits the control unit and patient valve to be very simple and robust devices, resistant to abuse and easily operated correctly by personnel with a minimum of training. Indeed it is these features of such devices that have led to their increasing use for longer term ventilation as when patients with impaired respiratory function are subject to extended transportation. However, medical opinion is not undivided about the merits of long-term ventilation with pure oxygen. Moreover such devices necessarily have a relatively high rate of oxygen usage so that their long-term use can lead to problems of oxygen source availability.

There is therefore a need to provide a compact and portable gas-powered resuscitator/ventilator device with the facility to deliver to a patient, selectively, pure oxygen, oxygen diluted with air, or air. An objective of the present invention is to meet this need but without significantly affecting the standards of robustness, portability, resistance to abuse and ease of operation at present available in devices capable only of delivering pure oxygen.

The type of gas-powered resuscitator/ventilator device here of interest divides into two main sub-types: the sub-type characterised by a low-force patient valve and that incorporates a control unit that generates pulses at a low pressure appropriate for direct delivery to the patient; and the sub-type characterised by a high-force patient valve and that incorporates a control unit that generates either high-pressure pulses or relatively low-pressure pulses that are only a small amount higher in pressure than the pulses to be delivered to the patient. The devices having a low-force patient valve use a low impedance (large bore conduit) connection between the control unit and the patient valve and can be vulnerable to malfunction in the presence of contamination, whereas the devices having a high-force patient valve can have a high impedance (small bore conduit) connection between the control unit and the patient valve. The high-force patient valve has a number of advantages from the point of view of reliability in addition to its ability to operate with a relatively high impedance connection to the control unit. U.S. Pat. No. 4,004,603 and its counterparts disclose a patient valve of this type. For convenience herein, devices having high-force patient valves will be called, shortly, "high-force devices".

Traditionally, in ventilators designed for long-term use in, say, a hospital, dilution of oxygen to a desired breathable gas composition—for instance, a 30/70 oxygen/air mixture having therefore about 45% oxygen content—is accomplished by use of an entrainment mixer. However, the application of such an entrainment mixer to a gas-powered resuscitator/ventilator of the type of interest is not straightforward because such mixers can be designed to give either a high mixing ratio or high pressure recovery, but not both simultaneously. If, therefore, the mixer is designed to achieve the desired oxygen dilution the pressure recovery will generally be insufficient to allow of the use of a high impedance downstream connection: in other words, if the mixer is incorporated in the control unit, the latter will not be able to output pulses able to drive a high-force patient valve through a high-impedance conduit. In this context "high-impedance conduit" is to be understood as meaning a conduit that at the maximum flow therethrough imposes a pressure drop of more than about 3.5 kPa (0.5 psi).

Accordingly, to maintain the advantages of the high-force device sub-type, an entrainment mixer if used to accomplish oxygen dilution must be located at the patient valve. However this leads to control problems because of the basic requirement, in a resuscitator/ventilator device of the type of interest, to be able to deliver pure oxygen when necessary, e.g. for resuscitation purposes. Thus it must be possible to disable the entrainment mixer, or to substitute a patient valve not having such a mixer, to provide for delivery of pure oxygen when this is required.

Selective disablement of an entrainment mixer at the patient valve, or the facility to exchange patient valves with and without entrainment mixers, respectively, leads to flow regulation problems because flow regulation is normally performed within the control unit by means of a high-impedance restriction that makes the output of the unit independent of the impedance characteristics both of the patient valve and of the conduit connecting the latter to the control unit, and also independent of patient compliance, over a wide range of values. If the flow regulation is set to deliver in accordance with the requirements of pure oxygen ventilation then, when a patient valve having an entrainment mixer is brought into operation to achieve dilution of oxygen delivered by the control unit, the oxygen delivery will be in excess of oxygen requirements and wastage will occur. That is to say, while the device in these circumstances delivers diluted oxygen as desired, its oxygen consumption will remain at the rate corresponding to usage of pure oxygen.

Accordingly it would appear that provision must be made at the control unit for resetting the flow regulation in accordance with the absence or presence at the patient valve of an operative entrainment mixer. This is obviously undesirable in a device that must be used, perhaps under adverse emergency conditions, by personnel with little training and/or who are called upon to use the device infrequently.

However, it has been discovered that it is in fact possible to avoid the apparent need for resetting of flow regulation arrangements at the control unit, by giving the patient valve impedance characteristics that affect the flow regulation function, appropriately to reduce oxygen delivery by the control unit, when there is an operative entrainment mixer at the patient valve.

SUMMARY OF THE INVENTION

The invention provides a gas-powered resuscitator/ventilator device of the type comprising a control unit having a high-impedance flow-regulation restriction adapted to output to a patient valve primary gas pulses appropriate for undiluted delivery to a patient. The patient valve includes an entrainment mixer than when operative dilutes primary gas pulses output by the control unit. The patient valve and the entrainment mixer, when this is operative, jointly provide a primary gas flow impedance so related to the impedance of the flow-regulation restriction of the control unit as to reduce primary gas flow therethrough.

Thus by simple substitution of the relatively low-impedance patient valve that would be appropriate to deliver undiluted primary gas—e.g. pure oxygen—by the patient valve and operative entrainment mixer combination, the flow-regulation at the control unit is automatically overridden, conveniently to the extent necessary to compensate for the reduced primary gas requirement of the patient valve and operative entrainment mixer combination.

The device of the invention may have two exchangeable patient valves—one of relatively low impedance and adapted to deliver to a patient undiluted primary gas pulses as received from the control unit, and another including a permanently operative entrainment mixer and of appropriately higher impedance—or the device may comprise a single patient valve incorporating an entrainment mixer that may be rendered operative or inoperative as required, by means that cause the impedance presented to primary gas flow to be appropriately raised when the entrainment mixer is rendered operative.

Thus, in an embodiment of the invention, a gas-powered resuscitator/ventilator device comprises a control unit having a high-impedance flow-regulation restriction adapted to output to a patient valve primary gas pulses appropriate for undiluted delivery to a patient, the patient valve including an entrainment mixer and a series flow restrictor, a shunt circuit and ganged valve means oppositely controlling diluent flow to the entrainment mixer and primary gas flow in said shunt circuit respectively.

By means of this arrangement, a required ventilation tidal flow of pure oxygen (the primary gas supplied by the control unit) can be obtained via both of the entrainment device and the shunt circuit in parallel, while the entrainment device is effectively disabled by the valve means preventing flow of diluent into the entrainment mixer. In this operating mode, the primary gas flow impedance of the patient valve will be low, relatively to the flow-regulation restriction, so that the output to the patient valve will be substantially independent of changes in downstream compliance. Alternatively, when the entrainment mixer is placed in its operative condition by setting said valve means to allow diluent to enter the entrainment mixer, the shunt circuit is closed by said valve means to prevent by-pass flow of primary gas (oxygen) therethrough, the impedance of the patient valve to primary gas flow being thereby raised to the extent necessary to limit the total flow of oxygen drawn from the control unit.

The restrictor associated with the entrainment mixer may conveniently be constituted by the nozzle thereof, because this arrangement offers the highest available pressure recovery, it being understood that the impedance offered by this restrictor is preferably selected to provide, in combination with the flow-regulation restriction of the control unit, no more than the appropriate flow of primary gas (oxygen) to provide, with dilution, the total ventilation tidal flow volume required by the patient. Thus, the impedance of the shunt circuit and of the mixer and associated restrictor may be so chosen that when the mixer is operative the impedance at the patient valve exceeds that obtaining when the mixer is disabled by an amount such that the primary gas flow to the patient valve is reduced in correspondence with the dilution of the primary gas to maintain a selected delivered gas volume.

While the invention is especially advantageously applicable to resuscitator/ventilator devices of the high-force sub-type to enable the reliability and other advantages of the high-force patient valve to be realized in conjunction with the ability to change, simply, from pure oxygen to diluted oxygen delivery, the invention may also be applied with advantage to devices of the low-force sub-type.

It should be understood that when flow through the shunt circuit is prevented in the operative condition of the entrainment mixer, the effective additional restriction of the primary gas (oxygen) flow path downstream of the control unit not only reduces the oxygen flow to the required value but also raises the oxygen pressure upstream of the entrainment mixer during the passage of a gas pulse, thereby to optimise the operation of the entrainment mixer and to provide a pressure/flow characteristic such that different patient airway resistances and lung compliances will have minimal effect upon the tidal flow volume delivered to the patient's lungs.

A resuscitator/ventilator embodying the invention has also the capability of delivering air pulses to a patient to assist breathing in circumstances in which oxygen enrichment of the delivered air is unnecessary or undesirable. Thus, by substituting a compressed air source for the normal oxygen source and using the entrainment mixer to "dilute" the air pulses thereby output by the control unit, air alone may be delivered. The compressed air source might, for instance, be a low power compressor.

The entrainment mixer may be of any suitable type. However it is preferred to employ an entrainment mixer of the construction described in co-pending Application Ser. No. 857,912 that allows the mixer to be of compact format without significant prejudice to its pressure-recovery capabilities.

BRIEF DESCRIPTION OF THE DRAWINGS

The invention is further explained with reference to the accompanying drawings. In the drawings.

DESCRIPTION OF THE ILLUSTRATED PRIOR ART, AND OF EMBODIMENTS OF THE INVENTION

Figure 1:
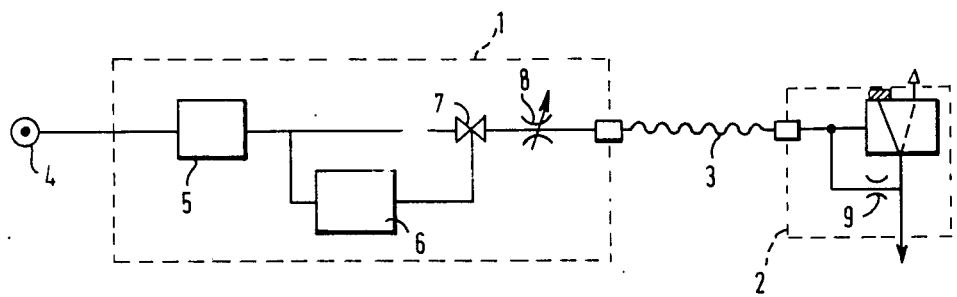
FIG. 1 is a diagrammatic representation of a typical gas-powered resuscitator/ventilator as currently known.

Referring to the drawings, FIG. 1 shows the basic components of a gas-powered resuscitator/ventilator device intended to deliver undiluted breathable gas—typically medical oxygen—from a source thereof to a patient for short-term forced ventilation. The device consists of two main units, a control unit 1 and a patient valve 2 connected by a flexible conduit 3. The arrangement illustrated is that for a device having a control unit that delivers pulses of gas at suitable pressure to a high-force patient valve, the conduit 3 constituting a high impedance connection between the control unit 1 and the patient valve 2 and consisting, for instance, in a flexible small bore hose.

The gas supply, that may for instance be from a cylinder of compressed oxygen and at a pressure in the range 250–600 kPa and typically 400 kPa (2.5–6 bar, typically 4 bar) is conventionally represented at 4 and is connected to a pressure regulator 5 that maintains a suitable output pressure (for instance 250 kPa (2.5 bar)) that is unaffected by variations in the gas supply pressure. The pressure regulator 5 may be external or, as represented, incorporated in the control unit. In either case, the control unit includes a timing unit 6 and associated valve 7 that when the control unit is in operation release suitably timed pulses of gas to a flow control valve 8. The timing unit 6 may for instance be a gas-powered oscillator, e.g. as disclosed in British Pat. No. 1,533,550.

The patient valve 2 may take a variety of forms, its function being to respond to the arrival of a gas pressure pulse over the conduit 3 to duct this pulse to the patient via an oronasal mask or intratracheal tube, while in the interval between such pulses the patient valve establishes communication between the patient and an exhalation port. The particular arrangement conventionally represented is that of a high-force patient valve of the construction described in U.S. Pat. No. 4,004,603, the restrictor shown at 9 being the internal flow path restriction that maintains a pressure differential between the gas pulse inlet and the gas pulse outlet of the valve while gas is flowing through the valve to the patient, thereby reliably to maintain the valve in the condition in which this flow path is open.

In a typical form of the system diagrammatically represented in FIG. 1, and in which the control unit 1 is intended to produce relatively low-pressure pulses, the flow control valve 8 is set to produce, at the required oxygen flow rate to deliver a pulse of the required tidal volume, a pressure drop, typically about 150 kPa (1.5 bar), that is a high percentage of the output pressure of the pressure regulator 5 so that minor impedance changes downstream of the valve 8, e.g. arising from variations in patient airway resistance and lung compliance, can have very little effect on the overall impedance downstream of the pressure regulator 5 and, hence, on the gas flow to the patient.

Figure 2:
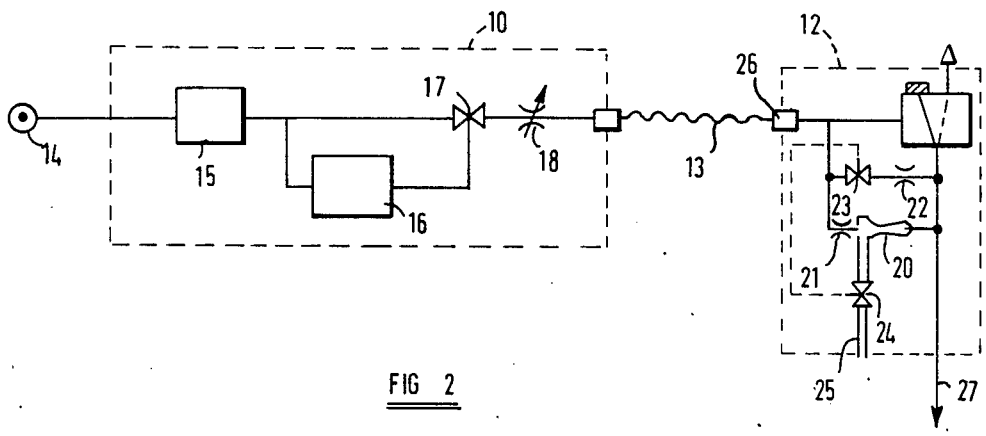
FIG. 2 is a diagrammatic representation of a gas-powered resuscitator/ventilator in accordance with one embodiment of the invention.

FIG. 2 illustrates an embodiment of the invention in which the control unit 10 may correspond in construction and arrangement with that of the device shown in FIG. 1, comprising a pressure regulator 15 providing, e.g., an output pressure of about 250 kPa (2.5 bar) as in the prior art arrangement of FIG. 1, a timing unit 16 and associated valve 17 together with a flow control valve 18. This control unit is intended to draw oxygen from a suitable source conventionally represented at 14 and to output pulses of oxygen via a conduit 13 that may conveniently be a high impedance conduit constituted by a flexible hose of relatively small bore.

In the system of FIG. 2, the patient valve represented at 12 includes an entrainment mixer 20 having an associated restrictor 21 in series and conveniently constituted by the nozzle of the mixer 20. The entrainment mixer 20 and restrictor 21 are bridged by a shunt circuit comprising a restrictor 22 and a valve 23 that is ganged with a valve 24 controlling a diluent inlet 25 for the entrainment mixer 20.

The ganged valves 23, 24 are so arranged that when valve 23 is open, valve 24 is closed, and vice versa.

Figure 3:
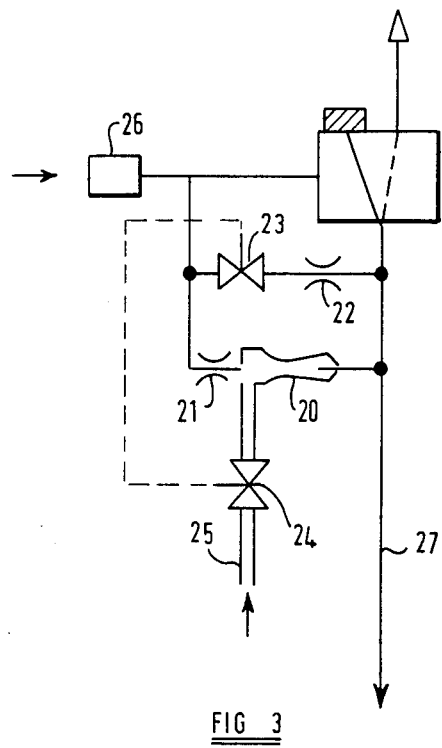
FIG. 3 is an enlarged schematic representation of the patient valve/entrainment mixer arrangement of the device of FIG. 2.

FIG. 3 shows, on a larger scale, the theoretical circuit of the patient valve 12 of FIG. 2. As in the case of FIG. 1, the illustration is that applicable to a patient valve of the high-force form and, depending on the operating condition, either the entrainment mixer 20 and its associated restrictor 21 (nozzle) constitute the flow path restriction between the gas pulse inlet and the gas pulse outlet of the valve of these devices with the restrictor 22 in parallel therewith constitute the said flow path restriction, for the purpose described.

In operation of the embodiment of FIGS. 2 and 3, when the resuscitator/ventilator device is to deliver pure oxygen pulses for forced ventilation of a patient, the ganged valves 23, 24 are set so that the valve 23 is open and the valve 24 is closed. Closure of the valve 24 prevents the entry of diluent (air) to the entrainment mixer 20 so that the pure oxygen pulses from the control unit 10, arriving at the gas pulse inlet 26, divide and flow through the shunt circuit with its restrictor 22 and through the entrainment mixer 20 and its associated restrictor 21 to the patient connection 27. The restrictors 21 and 22 are so sized, in relation to the impedance offered by the flow control valve 18 of the control unit 10, as to provide the requisite small pressure drop for holding the patient valve in its pulse-transmitting condition while passing the required ventilation tidal flow volume of oxygen to the patient. Because the impedance offered by the parallel restrictors 21 and 22 is small compared with that of the valve 18, and because of the non-linearity of the pressure drop/flow relationship of the restrictors 21, 22 and of the valve 18, it is the setting of the latter that effectively regulates the oxygen flow in this operating mode.

On the other hand, with the ganged valves 23, 24 set so that the valve 23 is closed and the valve 24 is open, the entrainment mixer 20 is enabled to receive diluent through diluent inlet 25, to be entrained in and mixed with the oxygen that passes through the mixer 20 and associated restrictor 21 (only) upon the arrival of an oxygen pressure pulse at the pulse inlet 26.

In this operating mode, because there is no flow in the shunt circuit comprising the restrictor 22, the effective impedance of the flow path between the pulse inlet 26 and the patient connection 27 is raised relative to that obtaining in the same flow path in the operating mode for delivery of pure oxygen to the patient connection 27. The consequence of this is that the oxygen flow in this operating mode is reduced, the non-linearity of the pressure drop/flow relationship for the restrictor 21 and for the valve 18 making the pressure drop at the restrictor 21 the more significant at this reduced flow rate and thus sharply transferring flow control from the valve 18 to the mixer 20 and restrictor 21 combination. By appropriate choice of impedance values for the mixer 20 and its associated restrictor 21, at the reduced flow rate required when the mixer 20 is operative, therefore, it can be arranged that in this operating mode the effective impedance at the patient valve so exceeds that of the flow control valve 18 as predominantly to control the flow rate at an amount such as to cause the oxygen flow in this mode to be approximately one-third of that in the operating mode in which the device delivers pure oxygen to the patient, while the mixer dilutes this oxygen with about twice its own volume of air to produce the same tidal flow volume as when delivering pure oxygen.

The valve 18 in a typical operational setting is equivalent to a throttle having a diameter of about 1.2 mm: in such configuration the restrictor 21 when constituted by the nozzle of the entrainment mixer would have a diameter of about 0.65 mm and the restrictor 22 a diameter of about 1.5 mm.

Thus, merely by suitable choice of impedance values, at the relevant flow rates, for certain components, the ventilation tidal flow volume required by a patient can be provided either wholly by oxygen or by a mixture of air and oxygen, with the oxygen flow and consumption being automatically reduced in the latter case merely as a consequence of bringing the entrainment mixer 20 into operation by actuation of the ganged valves 23, 24. That is to say, no adjustment of the flow control valve 18 at the control unit 10 is required on switching between delivery of pure oxygen, on the one hand, and delivery of diluted oxygen, on the other hand.

Moreover the components providing this selectable gas composition facility are either static (entrainment mixer 20, restrictors 21, 22) or of such simple mechanical form (ganged valves 23, 24) as to impose no reliability or other penalties upon the construction and use of the device in comparison with the equivalent device not having this additional facility.

Figure 4:
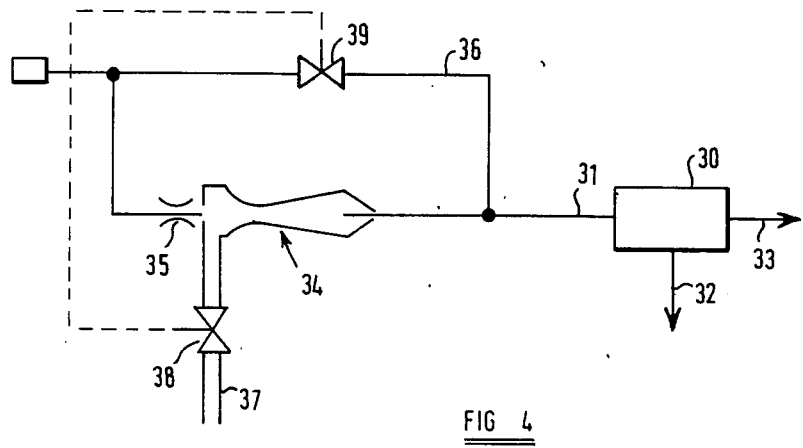
FIG. 4 corresponds with FIG. 3 but illustrates an embodiment in which the patient valve is of the low-force type.

As noted, the invention is also applicable to devices having low-force patient valves and FIG. 4 illustrates the theoretical circuit of the switchable entrainment mixer as applied to such a patient valve. In FIG. 4 the low-force patient valve is represented at 30 with its pulse inlet 31, patient connection 32 and exhalation port 33. In applying the invention, an entrainment mixer 34 with associated restrictor 35 and bridged by a shunt circuit 36 is arranged upstream of the pulse inlet 31. The entrainment mixer 34 has a diluent gas inlet 37 controlled by a valve 38 that is ganged with a valve 39 in the shunt circuit 36 so that when the valve 38 is open, the valve 39 is closed, and vice versa.

When the valve 39 is open there is effectively no impedance in the oxygen path to the pulse inlet 31 so that all gas flow control is exercised at the control unit in much the same way as in the arrangements illustrated in FIGS. 1 and 2. However, when the valve 39 is closed and the valve 38 is open, the impedance of the restrictor 35 appears in the oxygen flow path to the pulse inlet 31 and thus both reduces the oxygen flow while raising the upstream pressure to a value appropriate for correct functioning of the entrainment mixer 34.

In a convenient configuration for such an arrangement, the control unit would be arranged similarly to that of FIGS. 1 and 2 but with a flow control valve adapted to provide pulses at a pressure of about 0.5 kPa (5 mbar) when the valve 39 is open (and valve 38 closed) for delivery of pure oxygen to the patient. With the valve 39 closed (and valve 38 open) for delivery of diluted oxygen, the impedance of the mixer 34 and restrictor 35 (preferably constituted by the nozzle of the mixer) results in the pressure upstream of the restrictor 35 rising to approximately the delivery pressure of the pressure regulator of the control unit—say 250 kPa (2.5 bar) in the typical case.

Figure 5:
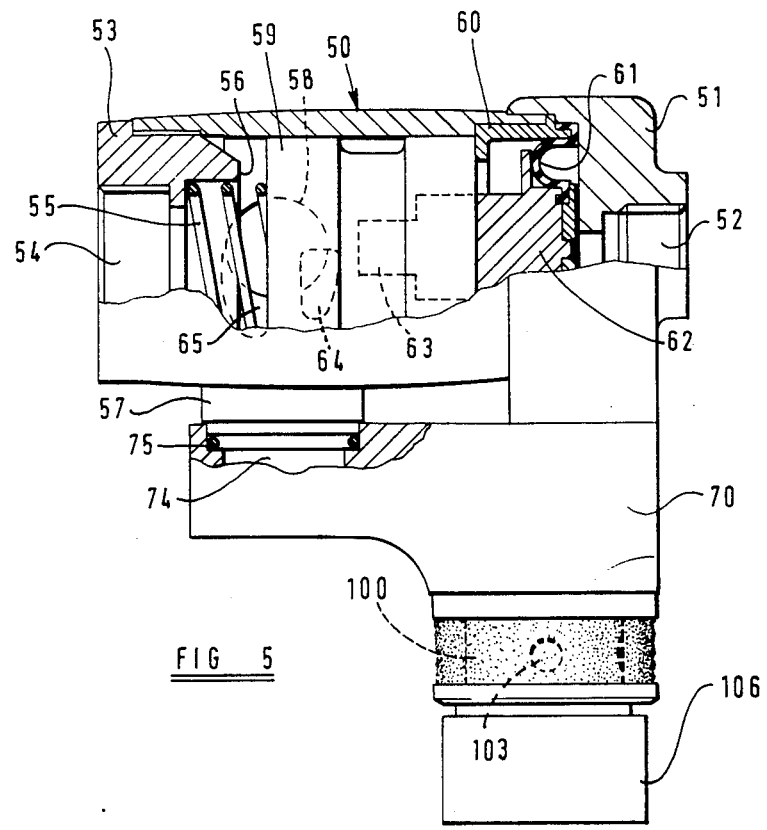
FIGS. 5, 6 and 7 illustrate a practical embodiment of a patient valve incorporating the arrangement of FIGS. 2 and 3, FIG. 5 being a part sectional side elevation, FIG. 6 a part sectional supply end elevation, and FIG. 7 a part sectional underneath plan.
Figure 6:
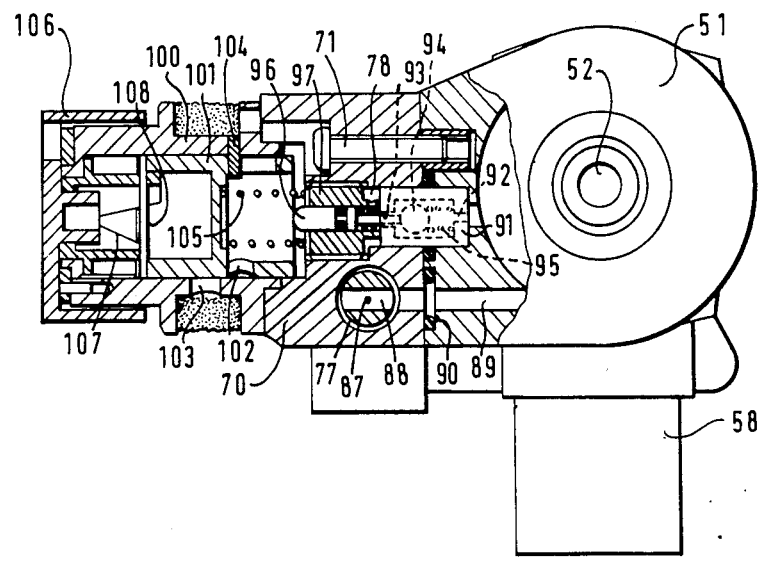
Figure 7:
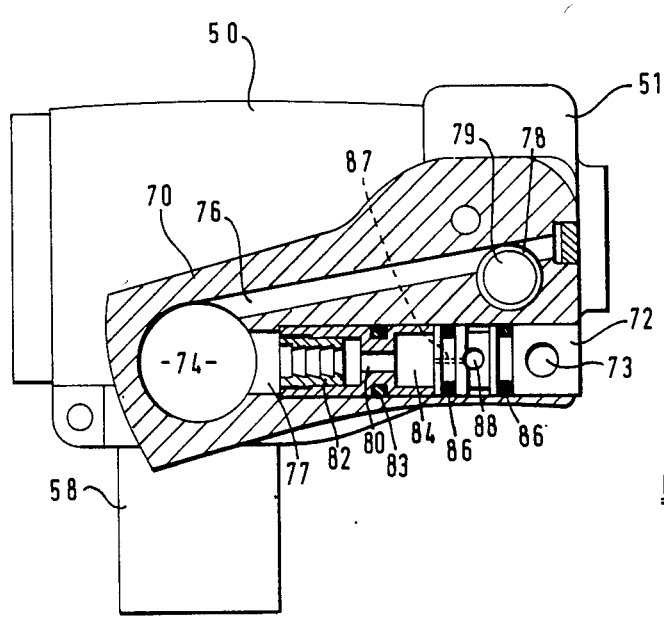

FIGS. 5 to 7 illustrate a practical realisation of the invention, in the form of a selectable output patient valve for a resuscitator/ventilator and conforming with the principles described in relation to FIGS. 2 and 3.

As shown in FIGS. 5 to 7, this realisation comprises a valve body part 50 defining a cylinder closed at a gas supply end by a cap 51 having an inlet port 52 for connection to a control unit that outputs pulses of primary gas, usually oxygen, in the manner described in relation to FIGS. 1 and 2. At the opposite, or exhalation end, the body part 50 has its cylinder closed by an annular plug 53 that provides an exhalation port 54 and a seating for a spring 55 within an annular valve seat 56.

The body part 50 is further comprised of a lateral gas transfer stub 57 and a patient connection stub 58 to receive a connecting tube for an oronasal mask or the like (not shown).

A waisted valve piston 59 is reciprocable within the cylinder of body part 50, being engaged by the spring 55 to be urged towards the gas supply end of the cylinder (to the right as seen in FIG. 5) and away from the valve seat 56.

The gas supply end of the cylinder accommodates a pilot assembly comprising a sleeve 60 located in a stepped bore portion of the cylinder and secured to the periphery of a flexible diaphragm 61 the central portion of which is secured to an operating plunger 62 having a spigot portion 63 engaged in a central recess in the piston 59.

The stubs 57 and 58 are interconnected within the body part 50, externally of the cylinder therein. The stub 57 has a connection to the cylinder via a port 64 in the wall of the cylinder and positioned to align with the waist of the piston 59 when the latter has moved to the left, as seen in FIG. 5, to engage the valve seat 56. The stub 58, on the other hand, connects with the cylinder via a port 65 positioned to be uncovered by the piston 59 when this is in the position illustrated, thereby to provide communication between the patient connection stub 58 and the exhalation port 54 in this position of the piston.

As so far described, the patient valve is functionally equivalent to the patient valve described in U.S. Pat. No. 4,004,603, differing in detail from the latter in that the piston 59 is driven by the pilot assembly diaphragm 61 in response to a gas pulse at the inlet port 52, rather than by gas acting directly on the piston, and in that gas entering the body part at port 52 reaches the patient connection stub by a restricted flow path external of the piston and cylinder, rather than through a restricted passage in the piston.

Thus, when a gas pulse arrives at port 52, the piston 59 is driven to the left as seen in the drawing, against the thrust of spring 55, to occlude the port 65 and to engage the valve seat 56 so as to isolate the patient connection stub 58 from the exhalation port 54. Under these conditions the gas pulse passes, by a route to be described, to the gas transfer stub 57 and thence to the stub 58 to flow to the patient and cause forced inhalation by the latter. When gas pulse pressure at the port 52 decays, the spring 55 returns the piston to the illustrated position to re-establish communication between the stub 58 and the exhalation port 54 so that the patient may exhale.

In accordance with the present invention, the gas flow path between the port 52 and the gas transfer stub 57 comprises an entrainment mixer that may be brought selectively into operation in such manner as automatically to adapt the primary gas flow to the required tidal volume of total supplied breathing gas.

Thus the patient valve further comprises a second body part 70 in the form of a plate that is secured to the body part 50 by bolts, one of which is shown at 71 (FIG. 6) and the other of which is not shown but is located to transfix and secure in place the jet block 72, described below, of the entrainment mixer by passing through a bore 73 in the jet block. The body part 70 has a plenum 74 that engages the gas transfer stub 57, being sealed thereto by an O-ring 75.

The body part 70 defines both a by-pass passage 76 and a mixer bore 77, both of which communicate with the plenum 74. The by-pass passage breaks tangentially into a chamber housing a poppet valve assembly 79 to be described below.

The mixer bore 77 houses the entrainment mixer that is constituted by the jet block 72, a receiver 80 and a pressure recovery section 81 comprising an insert 82 in the receiver body and having a substantially constant clear bore with steps defined by a succession of sharp-edged grooves. The mixer bore 77 is stepped near the plenum 74 to locate the end of the receiver body and the latter is sealed in the bore 77 by an O-ring 83. The receiver 80 is defined by an axial bore in the receiver body, communicating with an entrainment chamber 84 defined between wings 85 at the end of the receiver body and that serve to locate, by abutment, the jet block 72. The jet block 72 is also sealed in the mixer bore by a pair of O-rings 86 in grooves in the block 72. An axial jet passage 87 in the jet block extends to intercept a cross bore 88 in a waisted portion of the jet block 72 between the O-rings 86. As noted above, the jet block 72 is secured in the mixer bore 77 by a fixing bolt for the body part 70 extending through the bore 73 in the jet block. This fixing of the jet block also secures in place the receiver body that is effectively trapped between the jet block and a step in the mixer bore.

As best seen in FIG. 6, the waisted portion and cross bore 88 of jet block 72 communicate with a primary gas passage 89 formed partly in the body part 70 and partly in the end cap 51, this passage 89 communicating with the primary gas inlet port 52. An O-ring 90 provides a seal at the junction between the cap 51 and the body part 70.

The poppet valve assembly 79 comprises, as shown in FIG. 6, a valve constituted by a body 91 housed partly in the body part 70 and partly in the cap 51. The body 91 has an inlet 92 at one end and an outlet 93 at the other and houses a ball 94 and spring 95 controlling flow through the body 91. The inlet 93 communicates in the cap 51 with the primary gas inlet port 52.

The poppet valve assembly further comprises an actuating poppet 96 slidable in a guide 97 and sealed by O-rings. The poppet 96 has a spigot that extends into the outlet 93 of the valve body 91 to engage the ball 94 to unseat the latter when the poppet is moved to the right as seen in FIG. 6. When the ball 94 is so unseated, the by-pass passage 76 is placed in communication with the primary gas inlet port 52 via the chamber 78.

The patient valve further comprises a setting assembly (FIG. 6) comprising a barrel 100 secured to the body part 70 so that its axis is offset from that of the poppet valve assembly 79, the axis of the latter being near to the internal wall of the barrel 100. The barrel 100 houses a valve sleeve 101 having a ring of ports 102 and is slidable in the barrel to bring the ports 102 into and out of register with corresponding ports 103 in the barrel. The sleeve 101 is restrained from rotation by a pin 104 in the barrel running in a slot in the sleeve. A spring 105 acts to urge the sleeve 101 to the left, as see in the drawing, towards the position in which the ports 102 register with the ports 103.

The end of the sleeve 101 abuts the poppet 96 and the arrangement is such that when the sleeve is in the position shown, in which the ports 102 are out of register with the ports 103, the poppet is shifted to unseat the ball 94 of the poppet valve assembly. Conversely, when the sleeve 101 is positioned to register its ports with those of the barrel 100, the ball 94 is allowed to seat to interrupt communication between the primay gas inlet port 52 and the by-pass passage 76.

The setting assembly further includes a knob 106 rotatable with respect to the barrel 100 and carrying a cam 107 that acts on a cross pin 108 on the valve sleeve 101 to shift this against the thrust of the spring 105. The cam 107 is shaped to provide detent action to retain the knob in one or other of two relatively rotated positions, corresponding with the two required axially shifted positions of the valve sleeve 101.

The interior of the barrel 100 communicates, via a passage (not shown) in the body part 70, with the entrainment chamber 84 of the entrainment mixer. Thus, when the knob 106 is rotated to the position in which the valve sleeve ports 103 register with the barrel ports 102, the entrainment chamber 84 is placed in communication with the ambient atmosphere to enable diluent air to be drawn into the chamber 84 by entrainment action of the primary gas jet that issues from the nozzle 87 when a primary gas pulse is applied to the inlet port 52. In this setting of the knob 106, the poppet valve ball 94 is seated to prevent primary gas flow to the by-pass passage 76. Thus the primary gas is diluted en route to the plenum 74 and thence to the patient.

In this realisation of the invention, as compared with the theoretical diagrams of FIGS. 2 and 3, the nozzle 87 of the entrainment mixer corresponds with the restrictor 21 of FIGS. 2 and 3; the poppet valve assembly 79 corresponds with the valve 23; and the barrel 100 and sleeve 101, with their respective ports 102, 103, correspond with the valve 24. The restrictor 22 of FIGS. 2 and 3 has no direct counterpart but its function of providing, in parallel with the nozzle 87, a flow path impedance between the primary gas inlet port 52 and the plenum 74 sufficient to produce the pressure drop required to shift the piston 59 to close the exhalation port 54, against the action of spring 55, is accomplished by the flow path impedance attributable to the poppet valve assembly 79.

For certain purposes a device that can assist a patient to breathe air of normal oxygen content can be preferred to a device capable only of delivering oxygen or oxygen-enriched air. A resuscitator/ventilator embodying the invention can be adapted very simply to provide for delivery of pulses of air for such purposes. Thus, by substituting a source of compressed air for the described source of compressed oxygen, the control unit of such a resuscitator/ventilator would output air pulses, instead of oxygen pulses, to the patient valve. While such air pulses might be delivered direct to the patient, by the patient valve, in the same way as pure oxygen pulses would be delivered to the patient in one of the operating modes previously described, it is more advantageous to use the entrainment mixer to "dilute" the air delivered by the control unit, to provide the total breathable gas volume required, thereby minimising use of the compressed air source. In practice this means that a bottle of compressed air could provide for assisted breathing for a significant period, the air bottle supplying only about one third of the total breathing air required by the patient.

Moreover, because of the low demand on the compressed air source in such an operating mode, the compressed air source could be constituted by, for istance, a lightweight compressor capable of operation by a low power (e.g. 50 watt) electric motor drawing energy from a battery pack or umbilical lead to a vehicle battery to provide both portability and long term operation in the absence of bottled compressed air availability.

A resuscitator/ventilator embodying the invention can also provide other useful facilities, based upon its capability of inducing the admixture of a gas at ambient pressure with a primary gas supplied at pressure to power the device.

Thus, for instance, the gas made available for entrainment may be oxygen or oxygen-enriched air supplied, e.g., by an oxygen concentrator such as a molecular sieve concentrator. Accordingly the device may be caused to deliver to a patient a breathing gas consisting of oxygen-enriched air by being powered by compressed air as the primary gas and mixing this with oxygen or oxygen-enriched air, at about ambient pressure, supplied to the entrainment mixer of the patient valve. In a practical realisation of this operational possibility, and using a patient valve of the configuration described with reference to FIGS. 5 to 7, the ports 102 in the barrel 100 could be enclosed in a shroud fed with oxygen or oxygen-enriched air of suitable oxygen content output by, say, a molecular sieve oxygen concentrator.

In like manner, a primary gas constituted by compressed air or oxygen might be "diluted" at the patient valve with an anaesthetic gas or vapour supplied in suitable form to be entrained in the primary gas.

Thus, in principle a resuscitator/ventilator device embodying the invention may be powered by any suitable primary gas available under the required pressure and, with the aid of the entrainment mixer of the patient valve, deliver to the patient that primary gas "diluted" with any other "diluent" gas or vapour available at ambient pressure or thereabouts: the diluent being, for example, one or more of air, oxygen, water vapour, anaesthetic gas or vapour.

I claim:

1. In a gas-powered resuscitator/ventilator device comprising a control unit having a high-impedance flow-regulation restriction and means for providing undiluted primary gas pulse flow therefrom, a patient valve connected to said restriction and including first means having a specific impedance for delivering said undiluted primary gas pulse flow to a patient at a predetermined rate, the improvement comprising said patient valve also including a diluent gas entrainment mixer that when operative dilutes the primary gas pulse flow received from the control unit, the patient valve including second means operative with the entrainment mixer to jointly provide a flow impedance to the primary gas pulse flow such that the primary gas pulse flow combined with the entrained diluent gas flow is delivered to the patient at substantially the same predetermined rate as the undiluted primary gas pulse flow and means for selectively connecting either the first or second means to a patient.

2. The device of claim 1, in which, said second means of the patient valve and operative entrainment mixer combination is so related to the impedance of the flow-regulation restriction as to reduce the primary gas flow therethrough in correspondence with the dilution thereof by the entrainment mixer.

3. The device of claim 1, comprising a single patient valve incorporating an entrainment mixer that may be rendered operative or inoperative as required, by said second means that cause the impedance presented to primary gas flow to be appropriately raised when the entrainment mixer is rendered operative.

4. A gas-powered resuscitator/ventilator device comprising a control unit having a high-impedance flow regulation restriction and means for providing undiluted primary gas pulse flow therefrom; a patient valve connected to said restriction and including a shunt circuit having a specific impedance for delivering said undiluted primary gas pulse flow to a patient at a predetermined rate; a diluent gas entrainment mixer operatively associated with the patient valve that when operative dilutes the primary gas pulse flow received from the control unit; a flow restrictor in series with entrainment mixer such that the entrainment mixer and the flow restrictor present an impedance appropriate to restrict the primary gas pulse flow such that the primary gas pulse flow combined with the entrained diluent gas is delivered to a patient at substantially the same predetermined rate as the undiluted primary gas pulse flow through said shunt circuit and ganged valve means for selectively providing flow to the patient either through the shunt circuit or through the entrainment mixer.

5. The device of claim 4, in which the said restrictor in series with the entrainment mixer is constituted by the nozzle thereof.

6. The device of claim 4, in which the impedance of the shunt circuit and of the mixer and series restrictor are so chosen that when the mixer is operative the impedance at the patient valve exceeds that obtaining when the mixer is disabled, by an amount such that the primary gas flow to the patient valve is reduced in correspondence with the dilution of the primary gas to maintain a selected delivered gas volume.

7. The device of claim 5, in which the impedance of the shunt circuit and of the mixer and series restrictor are so chosen that when the mixer is operative the impedance at the patient valve exceeds that obtaining when the mixer is disabled, by an amount such that the primary gas flow to the patient valve is reduced in correspondence with the dilution of the primary gas to maintain a selected delivered gas volume.

* * * * *